United States Patent [19]

Mincher

[11] Patent Number: 5,733,880
[45] Date of Patent: Mar. 31, 1998

[54] ANTHRACENE DERIVATIVES FOR USE AS ANTICANCER AGENTS

[75] Inventor: David John Mincher, Dunbar East Lothian, United Kingdom

[73] Assignee: Napier University Ventures Limited, Edinburgh, England

[21] Appl. No.: 619,747

[22] PCT Filed: Sep. 30, 1994

[86] PCT No.: PCT/GB94/02128

§ 371 Date: Mar. 28, 1996

§ 102(e) Date: Mar. 28, 1996

[87] PCT Pub. No.: WO95/09149

PCT Pub. Date: Apr. 6, 1995

[30] Foreign Application Priority Data

Sep. 30, 1993 [GB] United Kingdom ............ 9320191

[51] Int. Cl.⁶ .................. A61K 38/00; C09B 1/16; C07C 46/00; C07C 50/18
[52] U.S. Cl. ............ 514/15; 552/238; 552/243; 552/247; 552/255; 552/268; 514/14; 514/16; 514/17; 514/18; 514/19
[58] Field of Search .................. 552/247, 268, 552/238, 243, 255, 256, 257, 258, 259; 514/12, 13, 14, 15, 16, 17, 18, 19; 550/260

[56] References Cited

U.S. PATENT DOCUMENTS

| 4,847,359 | 7/1989 | Pfeifer et al. |
| 4,855,084 | 8/1989 | Duthaler et al. |
| 4,894,451 | 1/1990 | Krapcho et al. |
| 4,924,015 | 5/1990 | Howell et al. |
| 4,927,865 | 5/1990 | Duthaler et al. |

FOREIGN PATENT DOCUMENTS

| 0 295 316 A2 | 12/1988 | European Pat. Off. |
| 0 298 031 A1 | 1/1989 | European Pat. Off. |
| 0 298 032 A2 | 1/1989 | European Pat. Off. |
| 0 489 220 A1 | 6/1992 | European Pat. Off. |
| 0489220A | 10/1992 | European Pat. Off. |
| 57-141456 | of 1982 | Japan. |
| WO 92/06670 | 4/1992 | WIPO. |
| WO 92/07557 | 5/1992 | WIPO. |
| WO 93/19037 | 9/1993 | WIPO. |

OTHER PUBLICATIONS

Pettit et al., "The coordination of copper (II) to 1-hydroxy-4-(glycyl-histidyl-lysine)-anthraquinone; a synthetic model of anthraquinone anti-cancer drugs.", Journal of Inorgaic Biochemistry, 45: 203–210, 1992.

Morier-Teissier, "Apport d'un peptide chelateur du cuivre a l'activite anticancereuse des anthraquinones.", J. Pharm. Belg., 45: 347–354, 1990.

Chemical Abstract, vol. 98, No. 8, p. 84, Feb. 21, 1983 (Abstract #98:55684e).

Morier-Teissier, E., et al., J. Med. Chem. 36 (15), 2084–2090, 1993.

Pettit, L.D., et al., J. Inorg. Biochem., 45, 203–210, 1992.

Morier-Teissier, E., J. Pharm. Belg., 45 (6), 347–354, 1990.

Bailly, C., et al. Bioconj. Chem., 2 (6), 379–393, 1991.

Morier-Teissier, E., et al., Journal of Biomol. Struct. & Dynamics, 9 (4), 653–666, 1992.

Morier-Teissier, E., et al., Anti-Cancer Drug Design, 5, 291–305, 1990.

Primary Examiner—José G. Dees
Assistant Examiner—Barbara Badio
Attorney, Agent, or Firm—Nixon, Hargrave, DeVans & Doyle

[57] ABSTRACT

A compound having the structural formula,

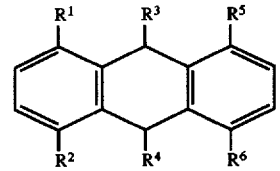

where $R^1$ and $R^2$ are independently hydrogen or hydroxyl. $R^2$ and $R^3$ are independently oxo or hydrogen, one of $R^5$ and $R^6$ is A—B and the other is hydrogen, hydroxyl, or a group A, wherein each A is a spacer group providing —NH— or —CO— in the bond with B (if present); at least one A group does not provide the residue of an α-amino acid adjacent the anthraquinone nucleus and the A of any A—B moiety is joined to the anthraquinone nucleus via an —NH— bond, and each B is a peptide group or a physiologically acceptable derivative thereof. The compounds are useful as antitumor compounds.

11 Claims, No Drawings

ANTHRACENE DERIVATIVES FOR USE AS ANTICANCER AGENTS

This application is a 371 of PCT/GB94/02128 filed Sep. 30, 1994.

The present invention relates to compounds which are based on an anthraquinone nucleus, for use in medicine or as dyes. The inhibition of DNA topoisomerases, particularly topoisomerase II (topo II) is now considered to be an important component in the mechanism of action of a large number of the most clinically active anticancer drugs presently available including doxorubicin, mitoxantrone, VP16, camptothecin, topotecan, M-AMSA, VM26 and the ellipticines. These drugs are believed to inhibit topo II by stabilising a protein/drug/nucleic acid ternary complex termed the clearable complex.

However, whilst targeting topoisomerases, these drugs also exhibit a number of other mechanisms of action, such as generation of free radicals and formation of DNA covalent adducts which contribute to their overall toxicity and poor therapeutic index. Additionally, the failure of these agents to produce long term cures in the major malignancies is probably exacerbated by the presence of de novo resistance and the development of acquired drug resistance.

U.S. Pat. No. 4,894,451 describes asymmetrically substituted anthracene-1,4-dione compounds of Formula (A):

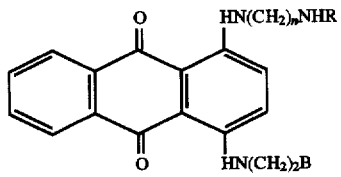

where B is a lower dialkyl amino group, n is 3–5 and R is hydrogen, alkanoyl or alkylsulphonyl. These compounds were proposed for use against tumours.

The co-pending WO 93/19037 describes compounds having the structural formula:

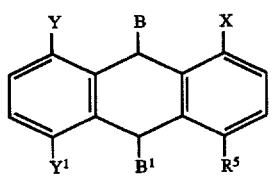

where Y and Y$^1$ are independently hydrogen or hydroxyl, B and B$^1$ are independently oxo or hydrogen, R$^5$ is hydrogen or hydroxyl and X is the residue of an α amino acid or a derivative of an α amino acid, joined to the ring shown via the nitrogen atom of the amino acid adjacent the acid group thereof. These compounds provide clinically active drugs and coloured compounds useful as drugs.

EP-A-0 295 316 discloses symmetrically-substituted compounds for use in anti-tumour therapy, namely 1,4-bis[(aminoalkyl- and hydroxyaminoalkyl)-amino]-5,8-dihydroxyanthraquinones.

A peptidic DNA-binding motif, the tetrapeptide SPKK (Ser-Pro-Lys-Lys) has been proposed (Suzuki (1989) *EMBO J*. 8, 797). SPKK dimers and hexamers were shown to compete with the AT-specific DNA-binding dye Hoechst 33258; nevertheless, they present a lower degree of specificity than Hoechst (Churchill & Suzuki (1989) *EMBO J*. 8, 4189; Suzuki (1989) *EMBO J*. 8, 797). Statistical studies suggested that SPKK forms a β-turn stabilized by an additional hydrogen bond between the Ser side chain OH group and the main chain NH group of the third residue Lys. A model was devised for the S$_2$ peptide, SPKKSPKK, in which the amides of Ser (the only amides to be free in the β-turn/Asx-turn mixed conformation) were relatively well overlapped onto the amides of netropsin known to form three centered hydrogen bonds with DNA. Thus, a succession of SPKK motifs may bind to AT-rich sequences in the minor groove by adopting a crescent shape similar to that of netropsin and also by using the same specific hydrogen bonds.

Bailly et al (1992) *Anti-Cancer Drug Design* 7, 83–100 describe anilinoacridine derivatives containing the nucleic acid-binding unit SPKK. The peptide is joined to the acridine heterocyclic ring system at the position opposite the N heteroatom in the middle ring.

A series of papers from Morier-Teissier et al [(1989) *Anti-Cancer Drug Design* 4, 37–52; ibid. (1990), 5, 291–305; (1993) *J Med Chem* 36, 2084–2090] disclosed various copper-chelating asymmetric peptide-anthraquinone compounds using a Gly-His-Lys moiety, or sometimes just the initial Gly, attached directly to the 4-position of the anthraquinone ring, with the 1-position being substituted by a hydroxyl group.

JP.A.82, 141456 describes N-[4-[(9,10-dihydro-9,10-dioxo-1-anthracenyl)amino]carbonyl]benzoyl]-D,L-alanine as a dyestuff.

Morier-Teissier et al (1993) *J. Med. Chem.* 36, 2084–2090 describes the synthesis of anthraquinone bisubstituted by the copper chelating peptide Gly-Gly-His.

It is an object of this invention to provide improved clinically active drugs. It is a further object of the invention to provide coloured compounds useful as dyestuffs.

In one aspect the invention provides a compound having the structural formula (I):

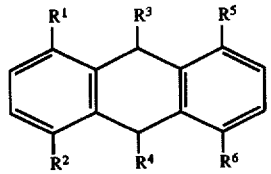

where R$^1$ and R$^2$ are independently hydrogen or hydroxyl, R$^3$ and R$^4$ are independently oxo, hydroxyl or hydrogen, one of R$^5$ and R$^6$ is A—B and the other is hydrogen, hydroxyl, or a group A, wherein, the or each A is independently a spacer group providing —NH— or —CO— in the bond with B (if present), at least one A group does not provide the residue of an α-amino acid adjacent the anthraquinone nucleus and the A of any A—B moiety is joined to the anthraquinone nucleus via an —NH— bond, and B is a peptide group;

or a physiologically acceptable derivative thereof.

Clearly, when R$^3$ or R$^4$ are oxo, the single line to the ring represents a double bond.

By a "spacer group" A we mean a bifunctional group providing either —NH$_2$ or —COOH at its extremities, but having an —NH— link to the ring.

It is preferred if a given spacer group is internally symmetrical as this avoids mixtures of products.

It is further preferred if the spacer groups are derived from α,ω-diamines. A α,ω-dicarboxylic acid can be used to extend the diamine group.

The α,ω-diamine may be an α,ω-diamino alkane. α,ω-Diamino alkanes include, for example $NH_2(CH_2)_nNH_2$ wherein n is 1 to 12, polyamines, for example diethylenetriamine $NH_2CH_2CH_2NHCH_2CH_2NH_2$ and chains including other heteroatoms for example $NH_2CH_2CH_2OCH_2CH_2NH_2$ or $NH_2CH_2CH_2SCH_2CH_2NH_2$.

Examples of suitable α,ω-diamines are shown in the table.

TABLE I

| α,ω-Diamine |
| --- |
| $H_2N(CH_2)_nNH_2, n = 2,3,4$ |
| $H_2N(CH_2)_nNH_2, n = 7,8,9$ |
| $H_2N(CH_2)_nNH_2, n = 5,6$ |
| $H_2N(CH_2)_2SS(CH_2)_2NH_2$ (cystamine) |
| $H_2N(CH_2)_2NH(CH_2)_2NH_2$ |
| $H_2N(CH_2)_2O(CH_2)_2NH_2$ |
| $H_2N(CH_2)_3NH(CH_2)_3NH_2$ |
| $H_2N(CH_2)_2NHCOCONH(CH_2)_2NH_2$ |
| $H_2N(CH_2)_2NH(CH_2)_2NH(CH_2)_2NH_2$ (TET) |
| $H_2N(CH_2)_3N(CH_2CH_2)_2N(CH_2)_3NH_2$ |

1,3-diaminopropane and 1,6-diaminohexane are preferred.

Other suitable diamines include those with alkene double bonds or saturated ring systems or substituted (para, ortho or meta) aryl groups. These provide conformationally restrained structures. For example cis and trans versions of $NH_2—(CH_2)_nCH=CH—(CH_2)_mNH_2$ and $NH_2(CH_2)_nC_6H_4(CH_2)_mNH_2$ (para, ortho or meta) and

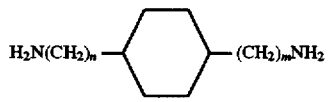

Conveniently m is 1–10 and n is 1–10. It is preferred if m=n.

α,ω-Dicarboxylic acids wherein the —$NH_2$ functional group of the aforementioned α,ω-diamines are replaced by —COOH are also useful in the present invention to extend the spacer group adjacent the ring. Suitable α,ω-dicarboxylic acids include succinic acid, malonic acid, fumaric acid, maleic acid and the like. The peptide is joined to such an extender group via a nitrogen, instead of an acid group, of an amino acid.

The peptide group B may be a single amino acid residue or an oligopeptide or polypeptide of up to 100 amino acid residues, preferably no more than 50, more preferably no more than 10 and especially 1, 2 or 3. The peptide group may contain spacer groups between the amino acids thereof. If present, such spacer groups are preferably selected from the same possibilities as group A and may alternate with the amino acid residues. The amino acids in the peptide group are preferably α-amino acids.

By "αamino acid", we mean any compound having a group

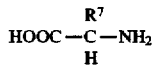

where $R^7$ is the residual group of an amino acid, for example hydrogen, straight or branched $C_{1-6}$ alkyl (such as methyl, isopropyl, 2-methylpropyl or 1-methylpropyl), hydroxyalkyl (such as —$CH_2OH$ or 1-hydroxyethyl), aralkyl (such as benzyl or 4-hydroxybenzyl), thiolalkyl (such as —$CH_2SH$), alkylthioalkyl (such as —$CH_2CH_2SCH_3$), acyl (such as —$CH_2COOH$ or —$CH_2CH_2COOH$), amidalkyl (such as —$CH_2CO.NH_2$ or —$CH_2CH_2CO.NH_2$) or linear or cyclic, aromatic or non aromatic, nitrogen-containing heterocyclic groups such as the groups forming pan of tryptophan, lysine, arginine or histidine.

We include all of the 20 α-amino acids commonly found in naturally-occurring proteins and their D-isomers; less common naturally-occurring α-amino acids found in proteins, such as 4-hydroxyproline, 5-hydroxylysine, desmosine, ε-N-methyllysine, 3-methylhistidine and isodesmosine and their D-isomers; naturally-occurring amino acids not found in proteins, such as β-alanine, γ-aminobutyric acid, homocysteine, homoserine, citrulline, ornithine, canavanine, djenkolic acid and β-cyanoalanine and their D-isomers; and di-, tri-, tetra-, penta-, oligo- or polypeptides based on these or other amino acids which peptides may optionally include non-amino acid residues or side elements such as sugar residues. For example, aspartic acid and glutamic acid can be incorporated containing lower alkyl, benzyl, or 4-nitrobenzyl esters as part of the side chain carboxyl group, or lysine and ornithine can contain carbobenzyloxy, tertiary-butyloxy, fluorenylmethoxycarbonyl protecting groups on the side-chain amino functionality, or arginine can be incorporated containing carbobenzyloxycarbonyl, tertiary-butyloxycarbonyl or nitro protection of the guanidinium functionality, or cysteine can be incorporated with tertiary-butyl or acetyl groups on the side-chain sulfhydryl group.

Thus, $R^7$ may be: hydrogen; straight or branched chain $C_{1-4}$ alkyl (for example methyl, isopropyl, isobutyl or sec-butyl); aryl-$C_{1-4}$-alkyl (for example benzyl, β-indolylmethyl, 4-hydroxybenzyl or 4-imidazolylmethyl); $C_{1-4}$-alkylthio-$C_{1-4}$-alkyl (for example methylthioethyl); hydroxy-$C_{1-4}$-alkyl (for example hydroxymethyl or 1-hydroxyethyl); mercaptomethyl (for example —$CH_2SH$); $C_{1-4}$ amide (for example —$CH_2C(O)NH_2$ or —$CH_2CH_2C(O)NH_2$); $C_{1-4}$ alkyl carboxylate (for example —$CH_2C(O)OH$ or —$CH_2CH_2C(O)OH$); $C_{1-6}$ alkylamine (for example $(CH_2)_4NH_2$); and imino($C_{1-6}$)alkyl-amine (for example —$(CH_2)_3NHC(=NH)NH_2$).

The di-, tri-, tetra-, penta-, oligo and polypeptides may be of any suitable amino acid sequence.

It is preferred if the peptide has the sequence (Ser-Pro-Lys-Lys)n wherein n is 1 to 10. It is further preferred if n is 1 to 6 and still further preferred if n=1 or 2.

Useful intermediates in the synthesis of Ser-Pro-Lys-Lys peptides include Nα-Z-Nε-BOC-L-lysyl-Nε-BOC-L-lysine methyl ester, Nε-BOC-L-lysyl-Nε-BOC-L-lysine methyl ester, Nα-Z-(O-t-butyl)-1-seryl-1-proline methyl ester, Na-Z-(O-t-butyl)-L-seryl-L-prolyl-Nε-BOC-L-lysyl-Nε-BOC-L-lysine methyl ester, Nα-Z-(O-t-butyl)-L-seryl-L-prolyl-Nε-BOC-L-lysyl-Nε-BOC-L-lysine, L-Seryl-L-prolyl-L-lysyl-L-lysine hydrobromide, Nα-BOC-(O-t-butyl)-L-seryl-L-proline methyl ester, Nα-BOC-(O-t-butyl)-L-seryl-L-proline, Nα-BOC-(O-t-butyl)-L-seryl-L-prolyl-Nε-BOC-L-lysyl-Nε-BOC-L-lysine methyl ester, Nα-BOC-(O-t-butyl)-L-seryl-L-prolyl-Nε-BOC-L-lysyl-Nε-BOC-L-lysine(O-t-butyl)-L-seryl-L-prolyl-Nε-BOC-L-lysyl-Nε-BOC-L-lysine methyl ester, Nα-BOC-[(O-t-butyl)-L-seryl-L-prolyl-ε-BOC-L-lysyl-ε-BOC-L-lysyl-ε-BOC-L-lysine]$_2$ methyl ester, Nα-BOC-[(O-t-butyl)-L-seryl-L-prolyl-ε-BOC-L-lysyl-ε-BOC-L-lysine]$_2$, (L-seryl-L-prolyl-L-lysyl-L-lysine)$_2$, hydrochloride. The syntheses of these compounds are described in detail in Bailly et al (1992) *Anti-Cancer Drug Design* (1992) 7, 83–100 incorporated herein by reference.

More generally, peptides may be synthesised by the Fmoc-polyamide mode of solid-phase peptide synthesis as disclosed by Lu et al (1981) *J. Org. Chem.* 46, 3433 and references therein. Temporary N-amino group protection is afforded by the 9-fluorenylmethyloxycarbonyl (Fmoc) group. Repetitive cleavage of this highly base-labile protecting group is effected using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethylacrylamide polymer constituted from the three monomers dimethylacrylamide (backbone-monomer), bisacryloylethylene diamine (cross linker) and acryloylsarcosine methyl ester (functionalising agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide/1-hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethanedithiol, phenol, anisole and water, the exact choice depending on the constituent amino acids of the peptide being synthesised. Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from Calbiochem-Novabiochem (UK) Ltd, Nottingham NG7 2QJ, UK. Purification may be effected by any one, or a combination of, techniques such as size exclusion chromatography, ion-exchange chromatography and (principally) reverse-phase high performance liquid chromatography. Analysis of peptides may be carried out using thin layer chromatography, reverse-phase high performance liquid chromatography, amino-acid analysis after acid hydrolysis and by fast atom bombardment (FAB) mass spectrometric analysis.

It will be appreciated by those skilled in the art that the peptide derivatives of the invention may be synthesised by chain extension on the spacer group or the peptide may be coupled to the spacer group once it has been synthesised.

Conveniently the anthroquinone nucleus is attached to a support and the spacer and amino acid added by solid phase synthesis.

By "derivatives" of the compounds of the invention, we include salts (acid or base addition), esters, amides, hydrazides and hydroxamic acids of the peptide group and other derivatives which do not diminish to an unacceptable extent the fundamental anti-turnout or colouring properties of the compounds.

Salts which may be conveniently used in therapy include physiologically acceptable base salts, for example, derived from an appropriate base, such as an alkali metal (eg sodium), alkaline earth metal (eg magnesium) salts, ammo-nium and $NX_4^+$ (wherein X is $C_{1-4}$ alkyl) salts. Physiologically acceptable acid salts include hydrochloride, sulphate, mesylate, besylate, phosphate and glutamate.

Salts according to the invention may be prepared in conventional manner, for example by reaction of the parent compound with an appropriate base to form the corresponding base salt, or with an appropriate acid to form the corresponding acid salt.

Especially preferred derivatives include those in which functional groups on the peptide group (which may be side groups or the terminal group) are capped and the terminal —NH— or —CO— on a spacer group which does not carry a peptide group is capped.

Suitable chemical groups to cap —NH— include H, —COCH$_3$, tertiary-butoxycarbonyl, benzyloxycarbonyl and other groups known in the art.

Suitable chemical groups to cap —CO— include —OH or any —O-linked or —N-linked radical, for example —O-alkyl, —O-benzyl, —O-alkylaminoalkyl, —O-alkoxyalkyl or —NH—NHR$^4$ wherein R$^4$ is straight or branched alkyl, optionally substituted by —CN or —OH, an amide group (such as —CONH$_2$) and other groups known in the art. Examples of alkylaminoalkyl groups include CH$_3$(CH$_3$)NCH$_2$CH$_2$—, —(CH$_2$)$_2$NH(CH$_2$)$_2$OH and CH$_3$(CH$_3$)NCH$_2$CH$_2$NHCH$_2$CH$_2$—.

By "alkyl", we include branched or straight chain alkyl of up to 20 carbon atoms, preferably 1–10 carbon atoms, more preferably 1–6 or 1–4 carbon atoms.

A useful discussion of alternative protective groups for amino acids (all types) and the scope of coupling reagents and deprotection reactions is to be found on pages 153–184 of a section called "chemical synthesis of peptides" in chapter 3 "Amino acids and Peptides" by R. S. Davidson and J. B. Hobbs in: "Natural Products, their Chemistry and Biological Significance", Authors: J. Mann, R. S. Davidson, J. R. Hobbs, D. V. Banthorpe & J. B. Harborne, publ. Longman Scientific and Technical (1994), incorporated herein by reference.

It has been found that the compounds of the invention may be prepared as substantially pure optical isomers.

Preferably B is a residue of alanine, phenylalanine, glycine, proline, valine, leucine, methionine, tyrosine or glycyl-glycine. The L-isomer is preferred in each case, although D-Phe is also preferred.

Preferably the capping entity is simply a hydrogen atom, an O-benzyl group or a tert-butoxy-carbonyl group.

Preferably R$^3$ =R$^4$ =oxo.

Preferably R$^1$ =R$^2$ =hydrogen.

Preferably A is 1,3-bisiminopropano, 1,4-bisiminobutano or 1,6-bisiminohexano.

It is further preferred that if B is a residue of Ala or Phe then A is 1,3-bisiminopropano or 1,6-bisiminohexano, the cap is hydrogen, R$^3$=R$^4$=oxo, and R$^1$=R$^2$=hydrogen.

Preferred sub-formulae of the invention are:

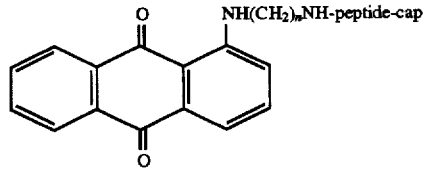

where n is 1 to 6, preferably 3, 4 or 6; "peptide" is a peptide of 1 to 5 amino acid residues, preferably only one or two; and "cap" one or more of is hydrogen, N-tBOC and O-benzyl; and

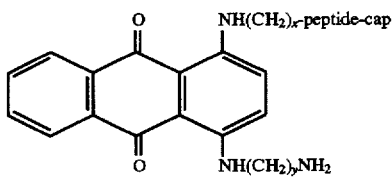

where x and y are independently 1 to 6, preferably 1, 2 or 3, and preferably x=y; and "peptide" and "cap" are as defined above in relation to formula (V).

A further aspect of the invention provides a process for preparing a compound of the invention comprising: a) reacting a compound of Formula (IV) (IV)

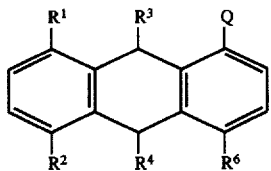

where Q is a reactive group such as —Cl or —Br, $R^3$=$R^4$= oxo and $R^1$ and $R^2$ are as defined above, with a compound A—B, wherein B is as defined above and A is a α,ω-diaminoalkane having a free —$NH_2$ group for coupling to the ring in compound (IV); (b) reacting a compound of Formula (IV)

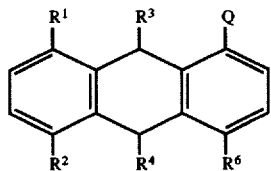

where $R^3$=$R^4$=Q=—OH and $R^1$=$R^2$=—H, with a compound A—B, wherein B is as defined above and A is an α,ω-diaminoalkane having a free-$NH_2$ group for coupling to the ring in compound (IV); (c) reacting a compound of Formula (IV)

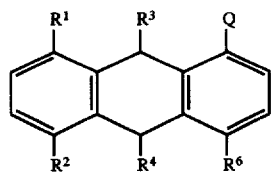

wherein Q is a group A as defined above and $R^1$ to $R^6$ are as defined above, with a compound B where B is a peptide as defined above, having an activated acid group on the α-amino acid which is to be coupled to spacer group A; or (d) conversion of one compound of Formula (I) to another compound of Formula (I). Referring to reaction (a) above, the compound of Formula (IV) is commercially available. The reaction generally proceeds in an aprotic solvent (eg DMSO or DMF). The amine (which can be used in excess) can form the solvent as well as being a reagent. The compound A—B used in reactions (a) and (b) may be made by reacting the α,ω-diaminoalkane spacer compound A with an activated acid derivative of peptide B, for example a pentafluorophenolate ester thereof, to form a complex primary amine. Reaction (b) generally proceeds in an inert atmosphere with excess primary amine above 50° C. for 1–2 hours, followed by cooling and aerial oxidation.

Similarly, in reaction (c) an activated acid derivative of the peptide B is reacted with the anthraquinone-spacer (mono- or disubstituted) compound. Compound (IV) and the activated, protected amino acid are reacted at 1:1 molar ratio in an inert solvent such as ethyl acetate, dichloromethane, chloroform or DMF, usually at −10.0° C. to room temperature (eg 0° C.) in an inert atmosphere. If A terminates in —COOH, it is activated (eg with pentafluorophenol), and coupled (eg with DCC, dicyclohexylcarbodiimide) to the N of an amino acid with a protected C terminus.

One compound of the invention can be converted to another by, for example, oxidising —H at $R^1$ and/or $R_2$ to —OH; oxidising —H at $R^3$ and/or $R^4$ to —OH; oxidising —OH at $R^3$ and/or $R^4$ to oxo, for example in an aerial oxidation or using chloranil; or reducing oxo at $R^3$ and/or $R^4$ to —OH (for example with sodium dithionite or zinc/acetic acid) or onward to —H. The sodium dithionite reaction is described in Marschalk et al (1936) *Bull. Soc. Chim. Fr.* 3, 1545, and the $Zn/CH_3COOH$ reaction in Morris, G. A. et at (1986) *Tetrahedron* 42, 3303. Another conversion of one compound of the invention to another involves extending the B group by removing any cap which is present and adding one or more amino acid residues.

Compounds of structure (II):

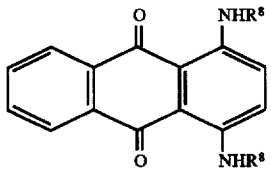

are readily available. $R^8$ is conveniently $X^1$—$NH_2$ wherein $X^1$ is —$CH_2$—$X^2$—$CH_2$—and $X^2$ is a divalent radical.

It is preferred if $X^1$ is —$(CH_2)_n$—$NH_2$ wherein n is 1 to 20, preferably 1 to 10, more preferably 1 to 5.

Compound (II) is readily synthesized from 1,4-dichloroanthroquinone and an appropriate diamine of structure $NH_2$—$X^1$—$NH_2$.

Alternatively, compound (II) can be made using compound (III):

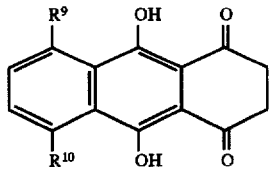

and aerially oxidizing within the presence of $R^8NH_2$.

Suitably $R^9$=$R^{10}$=OH or H. When $R^9$=$R^{10}$=H then compound (II) is leucoquinizarin and when $R^9$=$R^{10}$=OH then compound (II) is dihydroxyquinizarin.

Compounds of structure (II) can be readily synthesised from leucoquinizarin or dihydroxyquinizarin using the methods described in C. W. Greenhalgh and N. Hughes (1968) *J. Chem. Soc.* (C), 1284; K. C. Murdock et al (1979) *J. Med. Chem.* 2, 1024; and L. P. G. Wakelin et al (1987) *J. Med. Chem.* 30, 855, all incorporated herein by reference.

In a general scheme, the anthraquinone, di-substituted with spacer groups A, is dissolved in a solvent such as dimethylformamide containing an organic base such as triethylamine or diisopropylethylamine, or alternatively, in dry tetrahydrofuran in the presence of trimethylsilyl chloride and triethylamine. The solution is chilled, and to this is added the first amino acid, activated through its carboxyl group as its corresponding hydroxysuccinimide ester, or as the isobutyryl chloroformate, or as a mixed or symmetrical anhydride, or as any one of a number of carboxyl activating functionalities known to those skilled in the art of peptide synthesis. For the asymmetric compounds of the present invention, only one equivalent of the amino acid is added.

The α-amino group of the activated acid must be protected at this point by a group such as tertiary-butyloxycarbonyl, benzyloxycarbonyl, fluorenylmethoxycarbonyl, and the like, to avoid interference during condensation with the anthraquinones of this invention. Similarly, those amino acids which contain functionality in their side-chains in general also need to have the functionality protected, and are selected as described previously. The protecting groups used on the side chain can be the same or different than those used to protect the α-amino radical.

The activated, protected amino acid is dissolved in the same solvent used to dissolve the anthraquinone, and addition is done dropwise with stirring. The reaction is stirred at 0° to 40° C., preferably at room temperature, for about 24 hours, then filtered and the desired amide is isolated either by precipitation with a solvent of low polarity, or by evaporation. The protecting group on the α-amine is then removed such that elongation of the peptide chain can be achieved if desired. For example, the tertiary-butyloxycarbonyl group can be removed by dissolving the compound in anisole, cooling the solution in an ice bath and adding trifluoroacetic acid. The solution is stirred briefly in the cold, then warmed to room temperature for 1–24 hours. The desired deprotected product is isolated by diluting the reaction with a solvent in which the product is not soluble, for example diethyl ether, and the precipitate collected by filtration. Alternatively, the tertiary-butyloxycarbonyl group can be removed by dissolving the compound in a mixture of acetic acid and anisole, then hydrogen chloride gas is bubbled into the solution for a few minutes. After standing at room temperature for 1–24 hours, the absence of the compound is determined by a technique such as thin layer chromatography or analytical high pressure liquid chromatography, then the deprotected product is isolated by precipitation as described above. A benzyloxycarbonyl group can be removed by dissolving in a solvent such as acetic acid, cooling (but not freezing) the solution, and bubbling in gaseous hydrobromic acid. After the reaction has remained at room temperature for 1–24 hours and absence of starting material has been determined, the deprotected product is isolated by precipitation. Alternatively, the benzyloxycarbonyl group can be removed by hydrogenation of the protected compound in the presence of a noble metal catalyst such as palladium on carbon, but in this case re-oxidation of the reduced anthraquinone ring is generally necessary. A fluorenylmethoxycarbonyl group can be removed by dissolving the protected compound in a polar solvent such as dimethylformamide and adding a secondary amine such as dimethylamine. The deprotected product is again isolated either by precipitation or by evaporation of the reaction solution.

If desired, the next amino acid fragment is then added by repeating the sequence of reacting the deprotected compound with an α-amino and side-chain protected, carboxy group activated amino acid derivative, isolating the intermediate and removing the α-amino protecting group as described above. The process is repeated by judicious manipulation of the above conditions, or by applying conditions familiar to those skilled in the art of peptide synthesis until the entire desired peptide sequence has been assembled.

Alternatively, the entire peptide sequence can be assembled prior to formation of the amide bond between the peptide carboxy terminus and the anthraquinone nucleus. This can be accomplished by applying the solution techniques described above or assembling the peptide chain using any one of the techniques which have been developed as modifications of the Merrifield solid phase peptide synthesis procedure.

Removal of side-chain protecting groups, where desirable, and where these groups are the tertiary-butyloxycarbonyl, benzyloxycarbonyl or fluorenylmethoxycarbonyl radicals is accomplished as described above. In addition, the tertiary-butyloxy group required for protection of aspartic and glutamic acids is removed under the acid hydrolysis conditions described for cleavage of the tertiary-butyloxycarboxy protecting group. Most other groups are removed by slight modifications of the above-described procedures.

The starting materials where the spacer is hydroxyethyl-diaminoalkyl are described in U.S. Pat. No. 4,197,249.

In a further aspect the invention provides a pharmaceutical preparation comprising a pharmaceutically acceptable carrier and a compound of the above structure. Any suitable pharmaceutically acceptable carrier can be used. The preparation should be suitable for administration in the chosen manner. In particular, it should be sterile and, if intended for injection, non-pyrogenic.

The aforementioned compounds of the invention or a formulation thereof may be administered by any conventional method including enteral (for example oral and rectal) or parenteral (for example delivery into the nose or lung or injection into the veins, arteries, brain, spine, bladder, peritoneum, muscles or sub-cutaneous region. The compounds may be injected directly into the tumour. The treatment may consist of a single dose or a plurality of doses over a period of time. The dosage will be determined by the physician but may be between 0.01 mg and 1.0 g/kg/day, for example between 0.1 and 500 mg/kg/day. In terms of dose per square meter of body surface, the compound can be administered at 1.0 mg to 1.5 g per $m^2$ per day, for example 3.0–200.0 $mg/m^2$/day. At least some compounds of the invention have a particularly low toxicity to normal mammalian cells and could be given in quite high doses, for example 50–300 mg/kg. (Compare the doxorubicin maximum dose of 5 mg/kg in rodents and 1–2 mg/kg in man.)

Whilst it is possible for a compound of the invention to be administered alone, it is preferable to present it as a pharmaceutical formulation, together with one or more acceptable carriers. The carrier(s) must be "acceptable" in the sense of being compatible with the compound of the invention and not deleterious to the recipients thereof.

The formulations may conveniently be presented in unit dosage form and may be prepared by any of the methods well known in the art of pharmacy. A unit dosage form may comprise 2.0 mg to 2.0 g, for example 5.0 mg to 300.0 mg of active ingredient. Such methods include the step of bringing into association the active ingredient (compound of the invention) with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (eg povidone, gelatin, hydroxypropylmethyl cellulose), lubricant, inert diluent, preservative, disintegrant (eg sodium starch glycollate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Formulations suitable for parenteral administration include aqueous and non-aqueous sterile injection solutions which may contain anti-oxidants, buffers, bacteriostats and solutes which render the formulation isotonic with the blood of the intended recipient: and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

At least some of the compounds are useful as anticancer, antiviral and/or antiparasitic drugs and at least some of the anticancer compounds can be used against most malignancies.

Particular tumours suitable for treatment in accordance with the invention include leukaemias, and cancers of the uterine cervix, head, neck, brain gliomas, breast, colon, lung, prostate, skin, mouth, nose, oesophagus, stomach, liver, pancreas and metastatic forms of any of these.

Particular viral infections suitable for treatment in accordance with the invention include those caused by the viruses herpes simplex virus I (HSV I); herpes simplex virus II (HSV II); varicella-zoster virus/Ellen (VZV Ellen); bovine papilloma virus (BPV); and human immunodeficiency virus (HIV).

Particular protozoal infections suitable for treatment in accordance with the invention include trichomoniasis; malaria (especially that caused by *Plasmodium falciparum*); trypanosomiasis (caused by *Trypanosoma brucei* and *T. cruzi*); and leishmaniasis.

At least some of the compounds are useful as antibacterial agents.

At least some of the compounds are useful as dyestuffs and may be combined with a carder, diluent or mordant for dyeing purposes, for example for dyeing cotton, nylon and paper.

The following specific examples illustrate preferred, non-limiting compounds and processes of the invention.

EXAMPLE 1

Ligand synthesis: 1-[(6-Aminohexyl)amino]anthraquinone hydrochloride

1-Chloroanthraquinone (5 g, 0.0206 mol) was dissolved in 50 mL of DMSO and heated to reflux. 1,6-Diaminohexane (10 g, 0.086 mol) was added and kept under reflux for 5–10 min and the solvent was evaporated to dryness. The dark red residue was then dissolved in chloroform, washed twice with water, and extracted with a 10% aqueous solution of HCl. The acidic solution was then evaporated at low pressure and the residue was recrystallized from ethanol (yield 5.5 g, 74%) Anal. ($C_{20}H_{22}N_2O_2 \cdot HCl$) C, H, N, Cl.

EXAMPLE 2

Ligand synthesis: 1-[(12-Aminodecyl)amino]anthraquinone

This compound was prepared in the same fashion as the previous one. 1-Chloroanthraquinone (5 g, 0.0206 mol) and 18 g (0.09 moles) of 1,12-diaminododecane were refluxed in DMSO for 5–10 min. After evaporation of the solvent the pure product was obtained by column chromatography over alumina using chloroform, chloroform/MeOH 1:1 as eluent to yield 5.2 g (65%) of the free base. Anal. ($C_{26}H_{11}N_2O_3$) C, H, N.

The syntheses for the above compounds of Examples 1 and 2 are also described in Gibson et al (1991) *J. Med. Chem.* 34, 414–420.

1-(3-Aminopropyl)aminoanthraquinone hydrochloride and 1-(4-aminobutyl)-aminoanthraquinone hydrochloride can be prepared in analogous fashion as described in Katzhendler et al (1989) *Eur. J. Med. Chem.* 24, 23 incorporated herein by reference.

EXAMPLE 3

1-[3-(L-phenylalanyl-amino-propyl)-amino]-anthracene-9,10-dione

N-tertiarybutoxycarbonyl-L-phenylalanine (N-'Boc-Phe) [Novabiochem, Nottingham, UK], (326 mg, 1.23 mmol) and pentafluorophenol (252 mg, 1.36 mmol) were dissolved in ethyl acetate (8 ml) and the solution was stirred at 0° C. Dicyclohexylcarbodiimide (280 mg, 1.35 retool) dissolved in ethyl acetate (2 ml), was added and the resulting mixture was stirred for 30 min and then at room temperature for 1 h. The precipitated urea was filtered off and the filtrate evaporated to dryness. The crystalline residue of N-'Boc-L-phenylalanine pentafluorophenyl ester was used without further purification in the following coupling reaction.

The foregoing ester was dissolved in dimethylformamide (DMF) (6 ml) and the solution was added dropwise to a stirred solution of 1-[3-aminopropyl]aminoanthraquinone (308 mg, 1.1 mmol) in DMF (5 ml) at 0° C. under nitrogen. The mixture was allowed to attain room temperature and stirring was continued for 2 hr. Dimethylaminoethylamine (1 drop) was added to react with excess ester and after 10 min the solvent was evaporated in vacuo.

The residue was extracted into dichloromethane (25 ml) and the solution was washed with 10% citric acid (2×20 ml), 5% sodium hydrogen carbonate (2×20 ml) and water (20 ml) and then dried ($Na_2SO_4$) and evaporated to afford a red solid. The crude N-protected product was dissolved in trifluoroacetic acid-water (9:1) (25 ml) at room temperature. After 30 min the solvent was evaporated and the residue re-evaporated with methanol (3×10 ml). Ether was added and the resulting precipitate of the trifluoro acetate salt was filtered off. The salt was treated with triethylamine and taken up in toluene-ethyl acetate (4:1).

EXAMPLE 4
1-[3-(L-alanylaminopropyl)amino]-anthracene-9,10-dione

Prepared by an equivalent procedure to that described in Example 3 except that N-'Boc-Phe is replaced with N-tertiarybutoxycarbonyl-L-alanine (N-'BOC-Ala) [Novabiochem, Nottingham, UK].

m.p. 151° C. (decomp). Found C: 68.35; H: 5.75; N: 11.85%; M.351. Calc. C: 68.37; H: 5.98; N: 11.96%, $C_{20}H_{21}O_3N_3$ requires M.351. FAB(+) mass spectrum had m/z 352 ($M^+$+1).

EXAMPLE 5
1-[6-(L-alanylaminohexyl)amino]-anthracene-9,10-dione

Prepared by an equivalent procedure to that described in Example 4 except that 1-[6-aminohexyl]amino anthraquinone is used in place of 1-[3-aminopropyl]amino anthraquinine.

m.p. 146° C. Found C: 70.15, H: 6.75, N: 10.70%, M.393, Calc. C: 70.23, H: 6.87, N: 10.68%, $C_{23}H_{27}O_3N_3$ requires M.393. FAB(+) mass spectrum had m/z 394 ($M^+$+1).

EXAMPLE 6
1-[6-(L-phenylalanylaminohexyl)amino]-anthracene-9,10-dione

Prepared by an equivalent procedure to that described in Example 3 except that 1-[6-aminohexyl]aminoanthraquinone is used in place of 1-[3-aminopropyl] aminoanthraquinone.

m.p. 160° C. (decomp.). Found C: 74.15, H: 6.55, N: 8.80%, M.469, Calc. C: 74.20, H: 6.61, N: 8.95% $C_{29}H_{31}O_3N_3$ requires M.469, FAB(+) mass spectrum had m/z 470 ($M^+$+1).

EXAMPLE 7
1-[3-(N-tertiarybutoxycarbonylglycylaminopropyl)amino]-anthracene-9,10-dione Prepared by an equivalent procedure to that described in Example 3 except that N-'Boc-Phe is replaced with N-tertiarybutoxycarbonylglycine.

m.p. 188° C. Found C: 65.5; H: 6.10; N: 9.44%; M, 437, Calc. C: 65.90, H: 6.17; N: 9.61%. $C_{24}H_{27}O_5N_3$ requires M, 437.

FAB (+) mass spectrum had: m/z 438 ($M^+$+1); M, 437; 422 (M—$CH_3$).

$^1H$ nmr ($CDCl_3$) (270 MHz) had: δ1.42 (9H, s, 'BOC); 2.0 (2H, q $CH_2$); 3.45 (2H, q $CH_2$); 3.53 (2H, q, $CH_2$); 3.87 (2H, d, $CH_2$); 5.4 (1H, br s, N—H); 6.5 (1H, br s, N—H); 6.5 (1H, br s, N—H); 7.05 (1H, dd, H-2); 7.5–7.6 (2H, m, H-3 and H-4); 7.67–7.8 (2H, m, H-6, H-7); 8.24 (2H, m, H-5 and H-8); 9.73 (1H, t, N—H Ar). The i.r. spectrum [$v_{max}$, KBr, ($cm^{-1}$)] had: 3352, 3303 (NH); 1694 (C=O); 1668, 1650 (amide I and II); 1632, 1595 (quinone).

EXAMPLE 8
1-[3-(glycylaminopropyl)amino]-anthracene-9,10-dione

Example 7 is produced by standard N-deprotection of the glycyl residue in Example 6. The latter is dissolved in trifluoroacetic acid-water (9:1) at room temperature and the solvent evaporated after 30 min. The residue is re-evaporated with methanol and the title compound is obtained by recrystallisation from ethanol. Alternatively, the product may be isolated as its hydrochloride salt by precipitation from a solution of the compound in chloroform-ether at 0° C. upon passage of dry hydrogen chloride gas.

m.p. 213° C. Found C: 67.25; H: 5.48; N: 12.24%, Calc. C: 67.65; H: 5.64; N: 12.46%, M, 337, $C_{19}H_{19}O_3N_3$ requires M, 337.

FAB (+) mass spectrum had m/z 338 ($M^+$+1).

EXAMPLE 9
1-[3-(L-prolylaminopropyl)amino]-anthracene-9,10-dione

Example 9 is produced by an equivalent procedure to that described in Examples 3 and 8 except that N-tertiarybutoxycarbonyl-L-proline was used in place of N-tertiarybutoxycarbonyl-L-phenylalanine (Example 2), followed by N-deprotection.

m.p. 177–179% (decomp). Found, C: 69.85, H: 5.86; N: 10.96%, Calc. C: 70.0; H: 6.10; N: 11.14%, M, 377, $C_{22}H_{23}O_3N_3$ requires M, 377.

FAB (+) mass spectrum had m/z 378 ($M^+$+1).

EXAMPLE 10
1-[3-(L-valylaminopropyl)amino]-anthracene-9,10-dione

N-'Boc-L-valine is used in place of the N-'Boc-L-phenylalanine of Example 3, followed by N-deprotection.

m.p. 192° C. Found, C: 69.45; H: 6.48; N: 10.85%, Calc. C: 69.65; H: 6.59, N: 11.08%, M, 379, $C_{22}H_{23}O_3N_3$ requires M, 379.

FAB (+) mass spectrum had m/z 380 ($M^+$+1).

EXAMPLE 11
1-[3-L-leucylaminopropyl)amino]-anthracene-9,10-dione

Example 11 is produced by an equivalent procedure to that adopted for Example 3 except that N-tertiarybutoxycarbonyl-L-leucine was used in place of N-tertiarybutoxycarbonyl-L-phenylalanine, followed by N-deprotection.

m.p. 188°–190° C. Found, C: 69.85; H: 6.10; N: 10.56%, M, 393.

FAB (+) mass spectrum had m/z 394 ($M^+$+1).

EXAMPLE 12
1-[3-methionylaminopropyl)amino]-anthracene-9,10-dione

Example 12 is produced by an equivalent procedure to that described for Example 3 except that N-tertiarybutoxycarbonyl-L-methionine is used in place of N-tertiarybutoxycarbonyl-L-phenylalanine, followed by N-deprotection.

m.p. 156° C. (decomp). Found, C: 64.15; H: 5.86; N: 9.95%, M, 411, $C_{22}H_{25}O_3N_3S$ requires M, 411.

FAB (+) mass spectrum had m/z 412 ($M^+$+1).

EXAMPLE 13
1-[3-(O-benzyl-N-tertiarybutoxy-carbonyl-L-tyrosinylaminopropyl)amino]-anthracene-9,10-dione Example 13 is produced by an equivalent procedure to that described in Example 3 except that O-benzyl-N-tertiarybutoxycarbonyl-L-tyrosine was used in place of N-tertiary butoxycarbonyl-L-phenylalanine.

m.p. 248° C., Found, C: 71.96; H: 5.95; N: 6.55%, Calc. C: 72.05; H: 6.16; N: 6.63%, M, 633, $C_{38}H_{39}O_6N_3$ requires M, 633.

FAB (+) mass spectrum had m/z 634 ($M^+$+1), 618 (M—$CH_3$).

EXAMPLE 14

1-[3-(O-benzyl-L-tyrosinylaminopropyl)amino]-anthracene-9,10-dione

Example 14 was prepared by N-deprotection of Example 13 by an equivalent procedure to that described for Example 3.

m.p. 262° C., Found C: 74.02; H: 5.75, N: 7.74; M, 533, $C_{33}H_{31}O_4N_3$ requires M, 533.

FAB (+) mass spectrum had m/z 534 (M$^+$+1).

EXAMPLE 15

1-[3-(L-tyrosinylaminopropyl)amino]-anthracene-9,10-dione

The title compound was prepared by O-debenzylation of Example 14 by the following procedure:

1-[3-(O-benzyl-L-tyrosinylaminopropyl)amino-anthracene-9,10-dione (0.5 g) was dissolved in chloroform (40 ml) and cooled to −78° C. The solution was treated with boron trichloride (5 equivalents) and stirred at −78° C. for 10 min. The reaction mixture was allowed to warm up to −10° C. and was quenched by the gradual addition of water. The whole procedure was conducted under an argon atmosphere. A chloroform extract was washed several times with water, dried. (MgSO$_4$), filtered and evaporated to yield a crude red solid product. Analytically pure 1 -[3-(L-tyrosinylaminopropyl)amino]-anthracene-9,10-dione was obtained by thick-layer chromatography on silica gel plates followed by evaporation of the solvent (toluene-ethyl acetate 1:2) from the major fractions and recrystallisation of the residue from propan-2-ol-ether, in 63% yield.

m.p. 214° C. Found, C: 70.25; H: 5.54. N: 9.35%, M, 443. Calc. C: 70.43; H: 5.64; N: 9.48%, $C_{26}H_{25}O_4N_3$ requires M, 443.

FAB (+) mass spectrum had m/z 444 (M$^+$+1).

EXAMPLE 16

1-[4-(N-tertiarybutoxycarbonylglycylaminobutyl)amino]-anthracene-9,10-dione

The title compound was prepared by an equivalent procedure to that described for Example 3 except that the starting anthraquinone was 1-[(4-amino butyl)amino]-anthracene-9,10-dione (prepared from 1-chloroanthraquinone and 1,4-diaminobutane by an equivalent procedure to that adopted for Example 1); N-tertiarybutoxycarbonyl glycine replaced N-tertiarybutoxycarbonyl-L-phenylalanine. The produce was obtained in crystalline form from toluene.

m.p. 195. Found, C: 66.45; H: 6.15; N: 9.02%; M, 451, Calc. C: 66.52; H: 6.43; N: 9.31%, $C_{25}H_{29}O_5N_3$ requires M, 451.

FAB (+) mass spectrum had m/z 452 (25%) (M$^+$+1). $^1$H nmr (CDCl$_3$), (200 MHz) had: δ1.39 (9H, s, $^t$BOC 1.69 (4H, m, 2×CH$_2$); 3.23 (2H, q, CH$_2$N); 3.34 (2H, q, CH$_2$N); 3.78 (2H, d, CH$_2$ C=O); 5.4 (1H, br s, N—H exch. D$_2$O); 6.5 (1H, br s, NH exch. D$_2$O) 6.9 (1H, dd, H-2); 7.35–751 (2H, m, H-3 and H-4) 7.58–7.71 (2H, m, H-6 and H-7), 8.09–8.18 (2H, m, H:5 and H-8); 9.6 (1H, t, NHAr, exch. D$_2$O).

EXAMPLE 17

1-[(4-glycylaminobutyl)amino]-anthracene-9,10-dione

The title compound was prepared by trifluoroacetic acid mediated N-deprotection of Example 16 by an equivalent procedure to that described for Example 3.

m.p. 206° C. (deccomp). Found, C: 68.05; H: 5.75; N: 11.85% M, 351, Calc. C: 68.38; H: 5.98, N: 11.96%, $C_{26}H_{21}O_3N_3$ requires M, 351.

FAB (+) mass spectrum had m/z 352 (M$^+$+1). Example 18 1-[(3-N-tertiarybutoxycarbonyl-D-phenylalanylamino-propyl)amino]-anthracene-9,10-dione Example 18 was prepared by a procedure equivalent to that described for Example 3 except that N-tertiarybutoxycarbonyl-D-phenylalanine (Sigma Chemical Co., Poole, Dorset) replaced N-tertiarybutoxycarbonyl-L-phenylalanine and the starting anthraquinone was 1-[(3-amino propyl)amino]-anthracene-9,10-dione.

m.p. 168° C. Found, C: 70.25, H: 5.98; N: 7.75%, M, 527, $C_{31}H_{33}O_5N_3$ requires M, 527.

FAB (+) mass spectrum had m/z 528 (M$^+$+1).

EXAMPLE 19

1-[(4-N-tertiarybutoxycarbonyl-D-phenylalanylaminobutyl)amino]-anthracene-9,10-dione The title compound was prepared by an equivalent procedure to that adopted for Example 16 except that N-tertiarybutyloxycarbonyl-D-phenylalanine was used in place of N-tertiarybutoxycarbonylglycine.

m.p. 180° C. Found, C: 70.76; H: 6.25; N: 7.45%, M, 541, $C_{32}H_{35}O_5N_3$ requires M, 541.

FAB (+) mass spectrum had m/z 542 (8%) (M$^+$+1).

$^1$H nmr spectrum (CDCl$_3$, 200 MHz), had:

δ1.33 (9H, s, $^1$BOC); 1.54 (4H, m, unresolved 2×CH$_2$); 3.0 (2H, dd, CH$_2$Ph); 3.21 (4H, m, 2×CH$_2$NH); 4.27 (1H, q, CH); 5.12 (1H, br d, CH—NHCO, exch. D$_2$O); 5.91 (1H, br t, CH$_2$NHCO, exch. D$_2$O); 6.94 (1H, dd, H-2); 7.1–7.2 (5H, m, Ph); 7.42–7.55 (2H, m, H-3 and H-4); 7.59–7.73 (2H, m, H-6 and H-7); 8.13–8.22 (2H, m, H-5 and H-8); 9.6 (1H, t, NHAr, exch. D$_2$O).

EXAMPLE 20

1-[(4-D-phenylalanylaminobutyl)amino]-anthracene-9,10-dione

Example 20 was prepared by trifluoroacetic acid (standard) N-deprotection of Example 18 by a procedure equivalent to that described for Example 3.

m.p. 201° C. Found, C: 73.15; H: 5.94; N: 9.35%; M, 441, Calc. C: 73.47; H: 6.12; N: 9.52% $C_{27}H_{27}O_3N_3$ requires M, 441.

FAB (+) mass spectrum had m/z 442 (5%) (M$^+$+1).

EXAMPLE 21

1-[(3-N-tertiarybutoxycarbonyl-L-alanylaminopropyl) amino]-anthracene-9,10-dione.

Example 21 was prepared by an equivalent procedure to that described for Example 3 except that N-tertiarybutoxycarbonyl-L-alanine was used in place of N-tertiarybutoxycarbonyl-L-phenylalanine and the starting anthraquinone was 1-[(3-aminopropyl)amino]-anthracene-9,10-dione.

m.p. 214° C. Found, C: 66.35; H: 6.28; N: 9.25%, M, 451, Calc. C: 66.52; H: 6.43, N: 9.31%, $C_{25}H_{29}O_5N_3$ requires M, 451.

FAB (+) mass spectrum had m/z 452 (15%) (M$^+$+1).

$^1$H nmr (CDCl$_3$, 200 MHz), had:

δ1.32 (3H, d, CH$_3$); 1.36 (9H, s, $^t$BOC); 1.96 (2H, quintet, CH$_2$CH$_2$CH$_2$); 3.25–3.55 (4H, m, 2×CH$_2$N); 4.15 (1H, quintet, CH); 5.2 (1 t d, CHNHC=O, exch. D$_2$O); 6.63 (1H, t, CH$_2$NHC=O) 6.93 (1H, dd, H-2); 7.38–7.52 (2H, m, H-3 and H-4); 7.58–7.72 (2H, m, H-6 and H-7; 8.10–8.19 (2H, m, H-5 and H-8); 9.65 (1H, br.s. NHAr, exch. D$_2$O).

EXAMPLE 22

1-[(3-L-alanylaminopropyl)amino]-anthracene-9,10-dione

Example 22 was produced by trifluoroacetic acid mediated (standard) N-deprotection of Example 21 according to a procedure equivalent to that used in Example 3.

m.p. 232° C. Found, C: 68.05; H: 5.85, N: 11.65%, M, 351, Calc. C: 68.38; H: 5.98; N: 11.96% $C_{20}H_{21}O_3N_3$ requires M, 351.

FAB (+) mass spectrum had m/z 352 (5%) (M$^+$+1).

EXAMPLE 23

1-[(3-glycylglycylaminopropyl, amino]-anthracene-9,10-dione

The title compound was prepared according to an equivalent procedure to that used for Example 3, except that N-tertiarybutoxycarbonylglycylglycine (Novabiochem, Nottingham) replaced N-tertiarybutoxycarbonyl-L-phenylalanine and the starting anthraquinone was 1-[(3-aminopropyl)amino]-anthracene-9,10-dione. The title compound was obtained in crystalline form from aqueous ethanol after trifluoroacetic acid mediated (standard) N-deprotection of the first-formed coupling product.

m.p. 270° C. (decomp). Found, C: 63.82; H: 5.25; N: 13.85% M, 394, Calc. C: 63.96; H: 5.58; N: 14.21% $C_{21}H_{22}O_4N_4$ requires M, 394.

FAB (+) mass spectrum had m/z 395 (8%) (M$^+$+1).

EXAMPLES 24–29

Compounds disubstituted with spacer groups, only one of which carries a peptide group General procedure: The synthesis of the above was achieved by reaching the bis-substituted aminoalkylamino anthraquinones with one equivalent of the N-tertiarybutoxycarbonyl amino acid (after activation as its pentafluorophenolate ester) by an equivalent procedure to Example 3 to obtain the 1:1 adduct.

The bis-substituted aminoalkylamino anthraquinones are readily available and syntheses are given in the references relating to Formula (II) above.

EXAMPLE 24

4-[(2-aminoethyl)amino]-[(2-glycylaminoethyl)amino]-anthracene-9,10-dione

A solution of N-tertiarybutoxycarbonyl glycylpentafluorophenolate (0.89 g) [prepared from pentafluorophenol (0.48 g); dicyclohexylcarbodiimide (0.65 g) and N-$^t$Boc-glycine (0.46 g)] in ethyl acetate (15 ml) was added to a stirred solution of 1,4-bls [(2-aminoethyl)amino]-anthracene-9,10-dione, (0.85 g) in ethyl acetate (45 ml) at 0° C. under nitrogen. After 30 min the solution was allowed to reach room temperature and stirring continued for 16 h. Tlc revealed the presence of one major product spot Rf 0.2 (toluene:ethyl acetate 1:2, silica gel plates GF$_{254}$). The reaction mixture was washed successively with saturated sodium bicarbonate solution and water; the organic layer was then dried (MgSO$_4$) and evaporated to dryness. A solution of the residue (in the minimum toluene:ethyl acetate, 1:2) was applied to a silica gel column (3×25 cm) and eluted by the same solvent mixture. The fractions containing the major product were evaporated to a crystalline residue which was recrystallised from ethyl acetate. The product was shown by elemental analysis, mass spectroscopy [FAB (+) m/z 482 (M$^+$+1)] and $^1$H nmr spectroscopy (ratio of aromatic protons to tertiarybutyl protons) to be monoderivatised with glycine.

The foregoing N-tertiarybutoxycarbonyl derivative was suspended in trifluoroacetic acid-water (9: 1) for 30 min at room temperature, then diluted with water and extracted with chloroform. The chloroform extracts were washed with saturated sodium bicarbonate and water, then evaporated to a blue solid which was recrystallised from methanol to give the title compound.

m.p. 270° C. Found, C: 62.76, H: 5.95; N: 17.95%; M, 381, Calc. C: 62.99; H: 6.04; N: 18.37%, $C_{20}H_{23}O_3N_5$ requires M, 381.

FAB (+) mass spectrum has m/z 382 (M$^+$+1).

EXAMPLE 25

4-[(2-aminoethyl)amino]-1-[2-L-alanylaminoethyl)amino]-anthracene-9,10-dione

Example 25 was prepared by an equivalent procedure to that described for Example 24 except that N-tertiarybutoxycarbonyl-L-alanine was used in place of N-tertiarybutoxycarbonylglycine.

m.p. >250° C. Found, C: 63.65; H: 6.05; N: 17.56%, M, 395, Calc. C: 63.80; H: 6.33, N: 17.72%, $C_{22}H_{25}O_3N_5$ requires M, 395.

FAB (+) mass spectrum had m/z 396 (M$^+$+1).

EXAMPLE 26

4-[(2-aminoethyl)amino]-1-[(2-L-phenylalanylaminoethyl) amino]-anthracene-9,10-dione Example 26 was prepared by an equivalent procedure-to that described for Example 24 except that N-tertiarybutoxycarbonyl-L-phenylalanine was used in place of N-tertiarybutoxycarbonylglycine.

m.p. 263° C. Found, C: 68.52; H: 5.96; N: 14.75%; M, 471, Calc. C: 68.79; H: 6.16, N: 14.86%, $C_{27}H_{29}O_3N_5$ requires M, 471.

FAB (+) mass spectrum had m/z 472 (10%) (M$^+$+1).

EXAMPLE 27

4-[(3-aminopropyl)amino]-1-[(3-glycylaminopropyl) amino]-anthracene-9,10-dione

Example 27 was prepared by an equivalent procedure to that described for Example 24 except that the starting anthraquinone was 1,4-bis[(3-aminopropyl)amino]-anthracene-9,10-dione.

m.p. 269° C. Found, C: 64.45; H: 6.43; N: 16.92%, M, 409, Calc. C: 64.55; H: 6.60; N: 17.11%, $C_{22}H_{27}O_3N_5$ requires M, 409.

FAB (+) mass spectrum had m/z 410 (M$^+$+1).

EXAMPLE 28

4-[(3-aminopropyl)amino]-1-[(3-L-alanylaminopropyl) amino]-anthracene-9,10-dione Example 28 was prepared by an equivalent procedure to that described for Example 24 except that the starting anthraquinone was 1,4-bis[(3-aminopropyl)amino]-anthracene-9,10-dione and N-tertiarybutoxycarbonyl-L-alanine replaced N-tertiarybutoxycarbonylglycine.

m.p. 286° C. Found, C: 65.05; H: 6.52; N: 16.45%; M, 423, Calc. C: 65.25; H: 6.86; N: 16.55%, $C_{23}H_{29}O_3N_5$ requires M, 423.

FAB (+) mass spectrum had m/z 424 (5%) (M$^+$+1).

EXAMPLE 29

4-[(3-aminopropyl)amino]-1-[(3-L-phenylalanylaminopropyl)-amino]-anthracene-9,10-dione Example 29 was prepared by an equivalent procedure to that described for Example 24 except that the starting anthraquinone was 1,4-bis[(3-aminopropyl)amino]-anthracene-9,10-dione and N-tertiarybutoxycarbonyl-L-phenylalanine replaced N-tertiarybutoxycarbonylglycine.

m.p. 278° C. Found, C: 69.45; H: 6.54; N: 13.94%, M, 499, Calc. C: 69.74; H: 6.61; N: 14.03%, $C_{29}H_{33}O_3N_5$ requires M, 499.

FAB (+) mass spectrum had m/z 500 (5%) (M$^+$+1).

Biological Examples

The cytotoxic properties of selected examples were evaluated against a panel of established human tumour cell lines.

These included the following cell lines:

K562—a human chronic myelogenous leukaemia (Lozzio and Lozzio, 1975). HRT—18—a human primary adenocarcinoma from the human rectum (Tompkins et al, 1974).

DLD-1

HT-29 primary adenocarcinomas of the human colon.

HCT-18 (Fogh & Trempe 1975; Dexter et al, 1979)

HCLO

All cultures routinely maintained as monolayer cultures (with the exception of K562 which does not adhere strongly to plastic culture vessels) in RPMI 1640 culture medium supplemented with 10% foetal calf serum (heat inactivated at 56° C. for 20 min), penicillin/streptomycin (50 IU ml$^{-1}$), and Na pyruvate (1 mM), and buffered using HEPES.

Chemosensitivity in vitro was assessed using the microtetrazolium assay (MTT assay) (Twentyman & Luscombe, 1987).

Examples were soluble in 5% ethanol/saline. To each well, 20 μl of drug solution was added to give a final drug concentration of 0.1–100 μg/ml at four log increments. Solvent controls were used throughout, and the first row of each plate contained media plus drug in the absence of any cells. Each point is the result of three separate experiments and cytotoxic effects are expressed in terms of percent survival, taking the optical density of the control plates to represent 100% survival.

In vitro Chemosensitivity data, Examples 12; 15; 18; 20.

|  | $IC_{50}$ (μM) | | | |
|---|---|---|---|---|
| Cell Line | 12 | 15 | 18 | 20 |
| K562 | 17.2 | 14.2 | 19.8 | 22.8 |
| HCLO | 11.8 | 6.7 | 17.4 | 21.4 |
| HRT-18 | 10.4 | 3.0 | 7.7 | 16.8 |
| HT-29 | 7.8 | 0.6 | 2.5 | 14.2 |
| DLD-1 | 4.1 | 2.1 | 13.2 | 8.6 |

$IC_{50}$ values are the average concentrations of drug required to reduce the growth rate by 50% of the untreated control system.

Lozzio C. B. and Lozzio B. B. (1975) "Human chronic myelogenous leukaemia cell line with positive Philadelphia chromosome" *Blood* 45, 321.

Tompkins W. A. F. et al (1974) "Culture and antigenic properties of newly established cell strains derived from adenocarcinomas of the human colon and rectum" *Journal of the National Cancer Institute* 52, 1101.

Fogh J. and Trempe G. (1975) "New human tumour cell lines" in *Human Tumour in Vitro* Fogh J. (ed) page 119 Plenum Press, New York.

Dexter D. L. et al (1979) "N,N-dimethylformamide-induced alteration of cell culture characteristics and loss of tumorigenicity in cultured human colon carcinoma cells" *Cancer Research* 39, 1020.

Twentyman P. R., & Luscombe M. (1987) "A study of some variables in a tetrazolium dye (MTT) base assay for cell growth and chemosensitivity" *British Journal of Cancer* 56, 279.

The following examples illustrate pharmaceutical formulations according to the invention in which the active ingredient is a compound of any of the above structures.

EXAMPLE A
Tablet

| Active ingredient | 100 mg |
|---|---|
| Lactose | 200 mg |
| Starch | 50 mg |
| Polyvinylpyrrolidone | 5 mg |
| Magnesium stearate | 4 mg |
|  | 359 mg |

Tablets are prepared from the foregoing ingredients by wet granulation followed by compression.

EXAMPLE B
Ophthalmic Solution

| Active ingredient | 0.5 g |
|---|---|
| Sodium chloride, analytical grade | 0.9 g |
| Thiomersal | 0.001 g |
| Purified water to | 100 ml |
| pH adjusted to | 7.5 |

EXAMPLE C
Tablet Formulations

The following formulations A and B are prepared by wet granulation of the ingredients with a solution of povidone, followed by addition of magnesium stearate and compression.

Formulation A

|  | mg/tablet | mg/tablet |
|---|---|---|
| (a) Active ingredient | 250 | 250 |
| (b) Lactose B.P. | 210 | 26 |
| (c) Povidone B.P. | 15 | 9 |
| (d) Sodium Starch Glycollate | 20 | 12 |
| (e) Magnesium Stearate | 5 | 3 |
|  | 500 | 300 |

Formulation B

|  | mg/tablet | mg/tablet |
|---|---|---|
| (a) Active ingredient | 250 | 250 |
| (b) Lactose | 150 | — |
| (c) Avicel PH 101 ® | 60 | 26 |
| (d) Povidone B.P. | 15 | 9 |
| (e) Sodium Starch Glycollate | 20 | 12 |
| (f) Magnesium Stearate | 5 | 3 |
|  | 500 | 300 |

Formulation C

|  | mg/tablet |
|---|---|
| Active ingredient | 100 |
| Lactose | 200 |

Formulation C

| | mg/tablet |
|---|---|
| Starch | 50 |
| Povidone | 5 |
| Magnesium stearate | 4 |
| | 359 |

The following formulations, D and E, are prepared by direct compression of the admixed ingredients. The lactose used in formulation E is of the direction compression type.

Formulation D

| | mg/capsule |
|---|---|
| Active Ingredient | 250 |
| Pregelatinised Starch NF15 | 150 |
| | 400 |

Formulation E

| | mg/capsule |
|---|---|
| Active Ingredient | 250 |
| Lactose | 150 |
| Avicel ® | 100 |
| | 500 |

Formulation F (Controlled Release Formulation)

The formulation is prepared by wet granulation of the ingredients (below) with a solution of povidone followed by the addition of magnesium stearate and compression.

| | mg/tablet |
|---|---|
| (a) Active Ingredient | 500 |
| (b) Hydroxypropylmethylcellulose (Methocel K4M Premium) ® | 112 |
| (c) Lactose B.P. | 53 |
| (d) Povidone B.P.C. | 28 |
| (e) Magnesium Stearate | 7 |
| | 700 |

Drug release takes place over a period of about 6–8 hours and was complete after 12 hours.

EXAMPLE D

Capsule Formulations
Formulation A

A capsule formulation is prepared by admixing the ingredients of Formulation D in Example C above and filling into a two-pan hard gelatin capsule. Formulation B (infra) is prepared in a similar manner.

Formulation B

| | mg/capsule |
|---|---|
| (a) Active ingredient | 250 |
| (b) Lactose B.P. | 143 |
| (c) Sodium Starch Glycollate | 25 |
| (d) Magnesium Stearate | 2 |
| | 420 |

Formulation C

| | mg/capsule |
|---|---|
| (a) Active ingredient | 250 |
| (b) Macrogol 4000 BP | 350 |
| | 600 |

Capsules are prepared by melting the Macrogol 4000 BP, dispersing the active ingredient in the melt and filling the melt into a two-part hard gelatin capsule.

Formulation D

| | mg/capsule |
|---|---|
| Active ingredient | 250 |
| Lecithin | 100 |
| Arachis Oil | 100 |
| | 450 |

Capsules are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients a, b, and c using an extruder, followed by spheronisation of the extrudate and drying. The dried pellets are then coated with release-controlling membrane (d) and filled into a two-piece, hard gelatin capsule.

| | mg/capsule |
|---|---|
| (a) Active ingredient | 250 |
| (b) Microcrystalline Cellulose | 125 |
| (c) Lactose BP | 125 |
| (d) Ethyl Cellulose | 13 |
| | 513 |

EXAMPLE E

Injectable Formulation

Active ingredient 0.200 g

Sterile, pyrogen free phosphate buffer ($pH_{7.0}$) to 10 ml

The active ingredient is dissolved in most of the phosphate buffer (35°–40° C.), then made up to volume and filtered through a sterile micropore filter into a sterile 10 ml amber glass vial (type 1) and sealed with sterile closures and overseals.

EXAMPLE F

Intramuscular injection

| Active ingredient | 0.20 g |
|---|---|
| Benzyl Alcohol | 0.10 g |
| Glucofurol 75 ® | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (type 1).

EXAMPLE G

Syrup Suspension

| Active ingredient | 0.2500 g |
|---|---|
| Sorbitol Solution | 1.5000 g |
| Glycerol | 2.0000 g |
| Dispersible Cellulose | 0.0750 g |
| Sodium Benzoate | 0.0050 g |
| Flavour, Peach 17.42.3169 | 0.0125 ml |
| Purified Water q.s. to | 5.0000 ml |

The sodium benzoate is dissolved in a portion of the purified water and the sorbitol solution added. The active ingredient is added and dispersed. In the glycerol is dispersed the thickener (dispersible cellulose). The two dispersions are mixed and made up to the required volume with the purified water. Further thickening is achieved as required by extra shearing of the suspension.

EXAMPLE H

Suppository

| | mg/suppository |
|---|---|
| Active ingredient (63 μm)* | 250 |
| Hard Fat, BP (Witepsol H15 - Dynamit Novel) | 1770 |
| | 2020 |

*The active ingredient is used as a powder wherein at least 90% of the particles are of 63 μm diameter or less.

One fifth of the Witepsol $H_{15}$ is melted in a steam-jacketed pan at 45° C. maximum. The active ingredient is sifted through a 200 μm sieve and added to the molten base with mixing, using a silverson fitted with a cutting head, until a smooth dispersion is achieved. Maintaining the mixture at 45° C., the remaining Witepsol $H_{15}$ is added to the suspension and stirred to ensure a homogenous mix. The entire suspension is passed through a 250 μm stainless steel screen and, with continuous stirring, is allowed to cool to 40° C. At a temperature of 38° C. to 40° C. 2.02 g of the mixture is filled into suitable plastic moulds. The suppositories are allowed to cool to room temperature.

EXAMPLE I

Pessaries

| | mg/pessary |
|---|---|
| Active ingredient | 250 |
| Anhydrate Dextrose | 380 |
| Potato Starch | 363 |
| Magnesium Stearate | 7 |
| | 1000 |

The above ingredients are mixed directly and pessaries prepared by direct compression of the resulting mixture.

EXAMPLE J

Dyestuff 1.0 g of the compound of Example 1 is dissolved in 100 ml an aqueous solution of ethanol (50% v/v) and applied to a cotton web.

What is claimed is:

1. A compound having the structural formula (I):

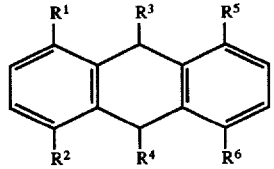

where $R^1$ and $R^2$ are independently hydrogen or hydroxyl, $R^3$ and $R^4$ are independently oxo, hydroxyl or hydrogen, one of $R^5$ and $R^6$ is A—B and the other is hydrogen, hydroxyl, or a group A, wherein, the or each A is independently a spacer group, other than A—B, providing —NH— or —CO— in the bond with B (if present), at least one A group does not provide the residue or an α-amino acid adjacent the anthraquinone nucleus and the A of the A—B moiety is joined to the anthraquinone nucleus via an —NH— bond, and B is a peptide group;

or a physiologically acceptable derivative thereof but excluding N-[4-[9,10-dihydro-9,10-dioxo-1-anthracenyl)amino]carbonyl]benzoyl]-D,L-alanine.

2. A compound according to claim 1 wherein A is an α,ω-bisiminoalkano group.

3. A compound according to claim 2 wherein the α,ωbisiminoalkano is 1,3-bisiminopropano, 1,4-bisiminobutyl or 1,6-bisiminohexano group.

4. A compound according to claim 1 wherein B is a residue of alanine, phenylalanine, glycine, proline, valine, leucine, methionine, tyrosine or glycylglycine.

5. A compound according to claim 1 wherein $R^1=R^2=H$.

6. A compound according to claim 1 wherein $R^3=R^4=$ oxo.

7. A compound according to claim 1 wherein the end and side chain functional groups of the or each amino acid in group B are capped with one or more of hydrogen, O-benzyl and N-tert-butoxycarbonyl.

8. A compound according to claim 1 wherein one of $R^5$ and $R^6$ is A—B and the other is A.

9. A pharmaceutical preparation comprising a pharmaceutically acceptable carrier and a compound having the structural formula (I):

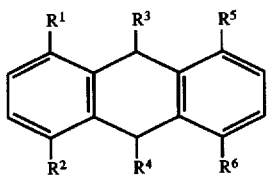

where $R^1$ and $R^2$ are independently hydrogen or hydroxyl, $R^3$ and $R^4$ are independently oxo, hydroxyl or hydrogen, one of $R^5$ and $R^6$ is A—B and the other is hydrogen, hydroxyl, or a group A, wherein, the or each A is independently a spacer group providing —NH— or —CO— in the bond with B (if present), at least one A group does not provide the residue of an α-amino acid adjacent the anthraquinone nucleus and the A of any A—B moiety is joined to the anthraquinone nucleus via an —NH— bond, and B is a peptide group;

or a physiologically acceptable derivative thereof.

10. A method of treating cancer in humans or mammals which comprises administering an effective amount of the compound as defined in claim 1 to the humans or mammals.

11. A process for preparing a compound according to claim 1 comprising (a) reacting a compound of Formula (IV)

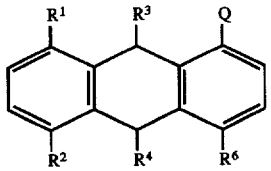

where Q is —Cl or —Br, $R^3$–$R^4$=oxo and $R^1$ and $R^2$ are as defined above, with a compound A—B, wherein B and $R^6$ are as defined above, and A is a α,ω-diaminoalkane having a free —NH₂ group for coupling to the ring in compound (IV);

(b) reacting a compound of formula (IV)

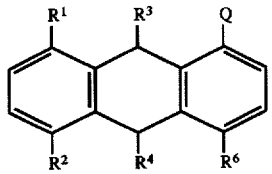

where $R^3$=$R^4$=Q=—OH and $R^1$=$R^2$=—H, with a compound A—B, wherein R and $R^6$ are as defined above, $R^6$ is a hydrogen, hydroxyl, or a group A, and A is an α,ω-diaminoalkane having a free —NH₂ group for coupling to the ring in compound (IV);

(c) reacting a compound of Formula (IV)

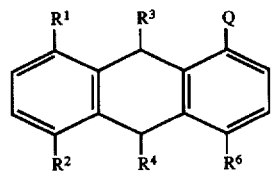

wherein Q is a group A as defined above and $R^1$ to $R^6$ are as defined above, with a compound D where B is a peptide as defined above, having an activated acid group on the α-amino acid which is to be coupled to spacer group A; or (d) conversion of one compound of Formula (I) to another compound of Formula (I) by oxidising —H at $R^1$ and/or $R^2$ to —OH; oxidising —H at $R^3$ and/or $R^4$ to —OH; oxidising —OH at $R^3$ and/or $R^4$ to oxo; reducing oxo at $R^3$ and/or $R^4$ to —OH or onward to —H; or extending B by removing any cap which is present and adding one or more amino acid residues.

* * * * *